(12) United States Patent
Efrati

(10) Patent No.: US 6,843,250 B2
(45) Date of Patent: Jan. 18, 2005

(54) METHOD AND SYSTEM FOR INTUBATION

(75) Inventor: Shai Efrati, Rishon Lezion (IL)

(73) Assignee: Hospitec Inc., Rishon Lezion (IL)

( * ) Notice: Subject to any disclaimer, the term of this patent is extended or adjusted under 35 U.S.C. 154(b) by 0 days.

(21) Appl. No.: 10/471,777

(22) PCT Filed: Mar. 21, 2002

(86) PCT No.: PCT/IL02/00230

§ 371 (c)(1),
(2), (4) Date: Feb. 3, 2004

(87) PCT Pub. No.: WO02/076279

PCT Pub. Date: Oct. 3, 2002

(65) Prior Publication Data

US 2004/0123867 A1 Jul. 1, 2004

(30) Foreign Application Priority Data

Mar. 23, 2001 (IL) .............................................. 142228

(51) Int. Cl.⁷ ........................................... A61M 16/00
(52) U.S. Cl. ........................... 128/207.14; 128/207.15; 128/207.18; 128/200.26; 128/205.23; 128/205.28; 128/204.22; 128/204.23; 600/529; 600/531; 600/538
(58) Field of Search ....................... 128/207.14, 207.15, 128/207.18, 200.26, 205.23, 205.28, 204.22, 204.23; 600/529, 531, 538

(56) References Cited

U.S. PATENT DOCUMENTS

| | | | |
|---|---|---|---|
| 3,504,676 A | | 4/1970 | Lomholt |
| 3,794,036 A | | 2/1974 | Carroll |
| 4,159,722 A | | 7/1979 | Walker |
| 4,305,392 A | | 12/1981 | Chester |
| 4,383,534 A | * | 5/1983 | Peters ........................ 600/484 |
| 4,501,273 A | | 2/1985 | McGinnis |
| 4,632,108 A | | 12/1986 | Geil |
| 4,691,701 A | * | 9/1987 | Williams ............... 128/207.14 |
| 4,770,170 A | | 9/1988 | Sato et al. |
| 4,825,862 A | | 5/1989 | Sato et al. |
| 4,850,371 A | | 7/1989 | Broadhurst et al. |
| 4,994,117 A | * | 2/1991 | Fehder ....................... 436/133 |
| 5,067,497 A | | 11/1991 | Greear et al. |
| 5,095,896 A | * | 3/1992 | Omoigui ................ 128/200.26 |

(List continued on next page.)

Primary Examiner—Henry Bennett
Assistant Examiner—Nihir Patel
(74) Attorney, Agent, or Firm—Ladas & Parry LLP

(57) ABSTRACT

An intubation method and system including the insertion of an endotracheal tube into a patient airway, inflating an cuff associated with the endotracheal tube at a location in the patient airway below the vocal cords, monitoring carbon dioxide concentration in the patient airway at a carbon dioxide monitoring location between the cuff and the vocal cords and adjusting inflation of the cuff based at least in part on the monitoring in order that the cuff inflation generally prevents leakage of carbon dioxide past the cuff.

22 Claims, 5 Drawing Sheets

U.S. PATENT DOCUMENTS

| | | | |
|---|---|---|---|
| 5,193,544 A | * 3/1993 | Jaffe | 600/323 |
| 5,197,464 A | * 3/1993 | Babb et al. | 128/207.14 |
| 5,251,619 A | * 10/1993 | Lee | 128/207.15 |
| 5,291,879 A | * 3/1994 | Babb et al. | 128/200.26 |
| 5,360,003 A | * 11/1994 | Capistrano | 128/207.15 |
| 5,579,762 A | 12/1996 | Lee | |
| 5,582,166 A | 12/1996 | Lee | |
| 5,582,167 A | 12/1996 | Joseph | |
| 5,622,182 A | * 4/1997 | Jaffe | 600/531 |
| 5,669,380 A | * 9/1997 | Garry et al. | 128/207.14 |
| 5,752,921 A | 5/1998 | Orr | |
| 5,765,559 A | 6/1998 | Kim | |
| 5,819,723 A | 10/1998 | Joseph | |
| 5,919,183 A | * 7/1999 | Field | 604/530 |
| 5,937,861 A | 8/1999 | Augustine | |
| 6,059,732 A | * 5/2000 | Orr et al. | 600/532 |
| 6,062,223 A | 5/2000 | Palazzo et al. | |
| 6,071,237 A | * 6/2000 | Weil et al. | 600/309 |
| 6,098,617 A | 8/2000 | Connell | |
| 6,135,105 A | * 10/2000 | Lampotang et al. | 128/204.21 |
| 6,568,388 B2 | * 5/2003 | Christopher | 128/200.26 |
| 2003/0172925 A1 | * 9/2003 | Zocca et al. | 128/202.22 |

* cited by examiner

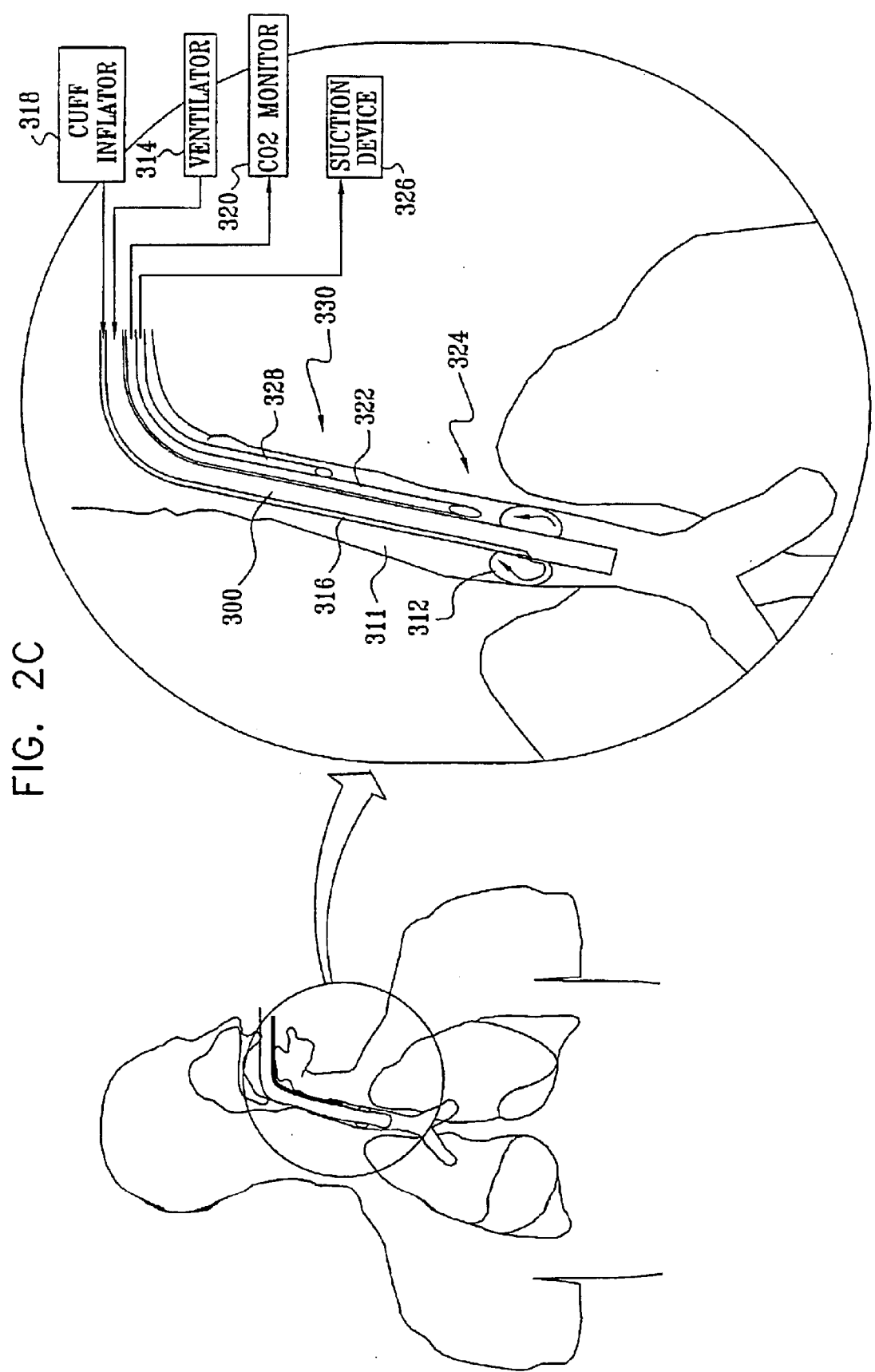

US 6,843,250 B2

METHOD AND SYSTEM FOR INTUBATION

FIELD OF THE INVENTION

The present invention relates to intubation systems and methodologies generally.

BACKGROUND OF THE INVENTION

The following U.S. Patents are believed to represent the state of the art: U.S. Pat. Nos. 6,062,223; 5,937,861; 5,819,723; 5,765,559; 5,752,921; 5,582,167; 5,582,166; 5,579,762; 5,067,497; 4,825,862; 4,770,170; 4,501,273; 4,305,392; 4,159,722; 3,794,036 & 3,504,676.

SUMMARY OF THE INVENTION

The present invention seeks to provide improvements to intubation systems and methods.

There is thus provided in accordance with a preferred embodiment of the present invention an intubation method including:

insertion of an endotracheal tube into a patient airway;

inflating a cuff associated with the endotracheal tube at a location in the patient airway below the vocal cords;

monitoring carbon dioxide concentration in the patient airway at a carbon dioxide monitoring location between the cuff and the vocal cords; and adjusting inflation of the cuff based at least in part on the monitoring in order that the cuff inflation generally prevents leakage of carbon dioxide past the cuff.

Preferably, inflation of the cuff is adjusted to provide a minimum inflation pressure, which prevents leakage of carbon dioxide past the cuff.

In accordance with a preferred embodiment of the present invention, the method also includes suctioning secretions at a suctioning location between the cuff and the vocal cords.

Preferably, the suctioning location is located between the cuff and the carbon dioxide monitoring location.

In accordance with a preferred embodiment of the present invention, adjusting inflation is performed by medical personnel based on information received from the carbon dioxide monitoring. Alternatively adjusting inflation may be performed automatically based on information received from the carbon dioxide monitoring.

Preferably, the method includes inserting into the patient airway of a carbon dioxide monitoring conduit extending to the carbon dioxide monitoring location.

Additionally or alternative, the method includes inserting into the patient airway of a suctioning conduit extending to the suctioning location.

The carbon dioxide monitoring conduit may also serve as a suctioning conduit extending to a suctioning location.

In accordance with one embodiment of the present invention, the insertion of an endotracheal tube into a patient airway includes insertion of at least one of a carbon dioxide monitoring conduit and a suctioning conduit disposed therewithin.

There is also provided in accordance with a preferred embodiment of the present invention an intubation system including:

an endotracheal tube adapted for insertion into a patient airway;

an inflatable cuff associated with the endotracheal tube and arranged to be located at a location in the patient airway below the vocal cords;

a carbon dioxide monitor operative to monitor carbon dioxide concentration in the patient airway at a carbon dioxide monitoring location between the cuff and the vocal cords; and an inflatable cuff inflator operative for enabling adjustment of inflation of the cuff based at least in part on an output from the carbon dioxide monitor in order that the cuff inflation generally prevents leakage of carbon dioxide past the cuff.

In accordance with one embodiment of the present invention, the inflator includes an adaptive inflator, which is operative to inflate the cuff to a minimum inflation pressure, which prevents leakage of carbon dioxide past the cuff.

Preferably, the system also includes a suctioner operative for suctioning secretions at a suctioning location between the cuff and the vocal cords.

In accordance with a preferred embodiment of the present invention, the system includes at least one of a carbon dioxide monitoring conduit coupled to the carbon dioxide monitor and extending therefrom to the carbon dioxide monitoring location and a suctioning conduit extending to a suctioning location.

In accordance with one embodiment of the present invention, the carbon dioxide monitoring conduit also serves as the suctioning conduit and also couples a suctioner operative for suctioning secretions to a suctioning location between the cuff and the vocal cords.

Alternatively a separate suctioning conduit may be provided for coupling a suctioner operative for suctioning secretions to a suctioning location between the cuff and the vocal cords.

At least one or both of the carbon dioxide monitoring conduit and the suctioning conduct may be located internally of the endotracheal tube.

BRIEF DESCRIPTION OF THE DRAWINGS

The present invention will be understood and appreciated from the following detailed description, taken in conjunction with the drawings in which:

FIGS. 2A, 2B, 2C and 2D are simplified diagrammatic illustrations of four alternative embodiments of the system of FIG. 1.

DETAILED DESCRIPTION OF PREFERRED EMBODIMENTS

Figure 1:
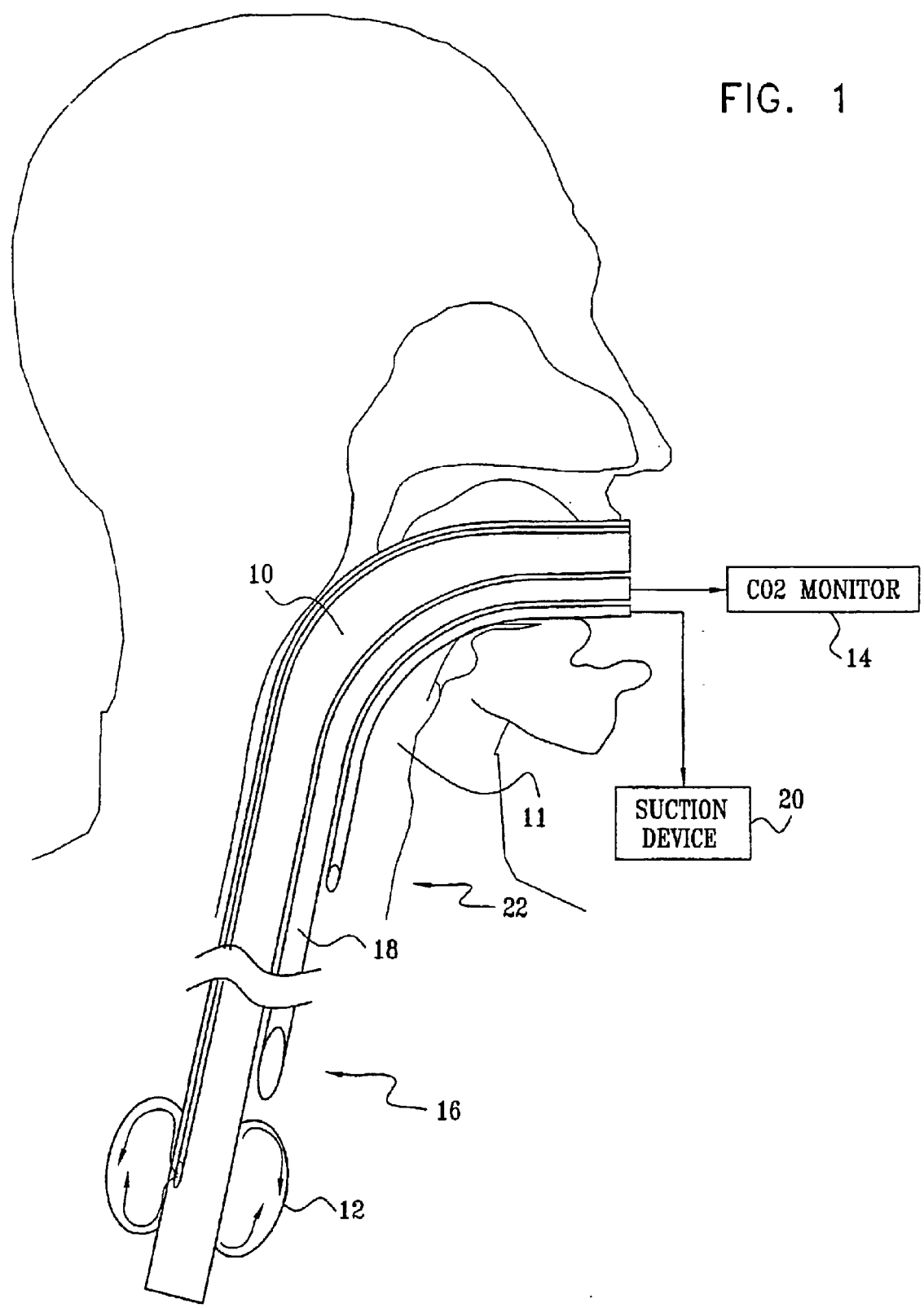
FIG. 1 is a simplified pictorial illustration of a intubation system and functionality constructed and operative in accordance with a preferred embodiment of the present invention.

Reference is now made to FIG. 1, which is a simplified pictorial illustration of an intubation system and functionality constructed and operative in accordance with a preferred embodiment of the present invention.

As seen in FIG. 1, there is preferably provided an intubation system and method wherein an endotracheal tube 10 is inserted into a patient airway. An inflatable cuff 12 is preferably associated with the endotracheal tube 10 and arranged to be located at a location in the patient airway 11 below the vocal cords. Both the endotracheal tube 10 and the inflatable cuff 12 may be entirely conventional or alternatively may be adapted to integrate features of the present invention, as described hereinbelow. The endotracheal tube 10 may be coupled to a ventilator (not shown) in a conventional manner and the inflatable cuff 12 may be connected to a manually operated or automatically operated inflation device (not shown), also in a conventional manner.

In accordance with a preferred embodiment of the present invention a carbon dioxide monitor 14 is provided and is operative to monitor carbon dioxide concentration in the patient airway 11 at a carbon dioxide monitoring location 16 between the cuff 12 and the vocal cords. Preferably a carbon dioxide monitoring conduit 18 is provided for coupling the monitor 14 to the monitoring location 16.

A suctioning device 20 is preferably provided for suctioning secretions at a suctioning location 22 between the cuff 12 and the vocal cords.

It is a particular feature of the present invention that the carbon dioxide monitor 14 provides an accurate indication of adequate sealing of the patient's airway 11 by the inflated cuff 12, thus enabling minimum effective inflation to be provided, thereby to minimize damage to the patient's airway 11. The accurate and minimally invasive sealing of the patient's airway 11 combined with operation of suctioning device for removal of secretions at suctioning location 22 upstream of the cuff 12 enables infections to be reduced by effectively preventing such secretions to enter the airway 11 downstream of the cuff 12. This effective preventing is the result both of highly effective sealing of the airway 11 and of removal of such secretions upstream of the cuff 12. It is appreciated that the efficacy of the suction produced by suctioning device 20 at suctioning location 22 is enhanced by the provision of highly effecting sealing of the airway at cuff 12.

It is appreciated that in accordance with one embodiment of the invention, the cuff inflator may operate automatically based on an accurate output from the carbon dioxide monitor.

Figure 2A:
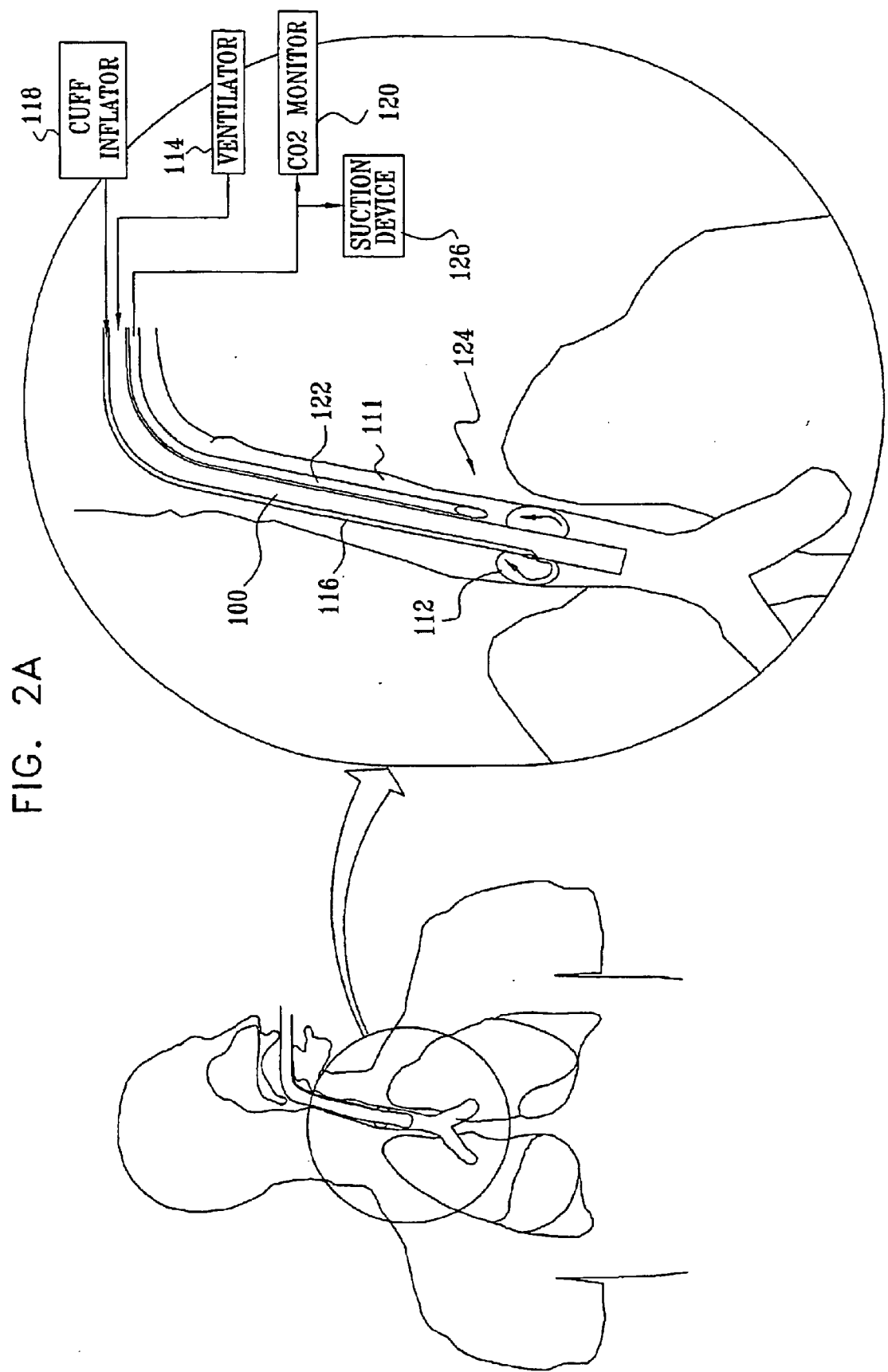

Reference is now made to FIGS. 2A, 2B, 2C, 2D are simplified diagrammatic illustrations of four alternative embodiments of the system of FIG. 1. Turning to FIG. 2A, there is seen a first embodiment of the invention wherein an endotracheal tube 100 is inserted into a patient airway 111 and an inflatable cuff 112, associated therewith and inflated at a location in the patient airway 111 below the vocal cords. The endotracheal tube 100 is typically, but need not be, coupled to a ventilator 114. Cuff 112 is connected via an inflation conduit 116 to a manually operated or automatically operated cuff inflator 118.

In accordance with a preferred embodiment of the present invention shown in FIG. 2A, a carbon dioxide monitor 120 is coupled via a carbon dioxide monitor conduit 122, external of the endotracheal tube 100, to a carbon dioxide monitoring location 124, between the cuff 112 and the vocal cords. A suctioning device 126 is also coupled to the conduit 122 for suctioning secretions at a suctioning location, which in this embodiment is identical to the carbon dioxide monitoring location 124.

Figure 2B:
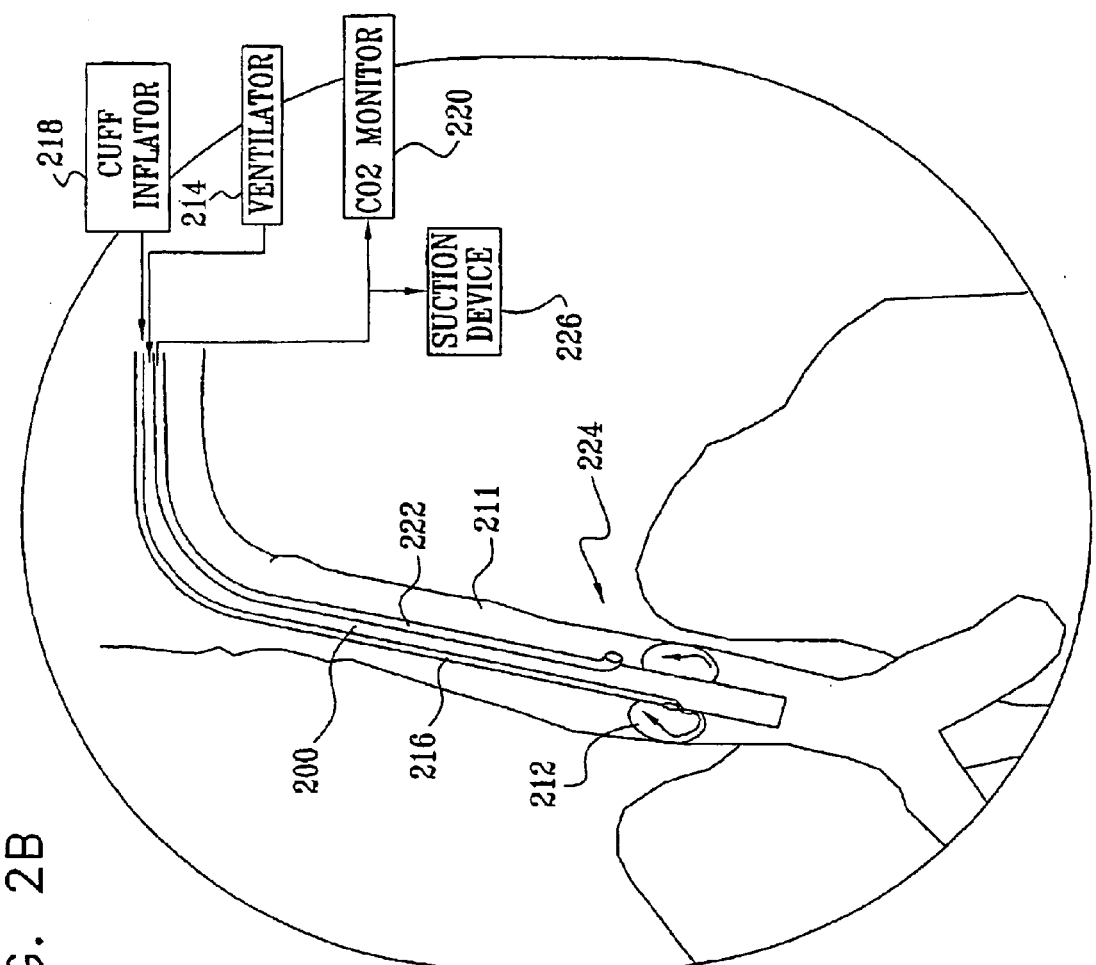
Figure 2B:
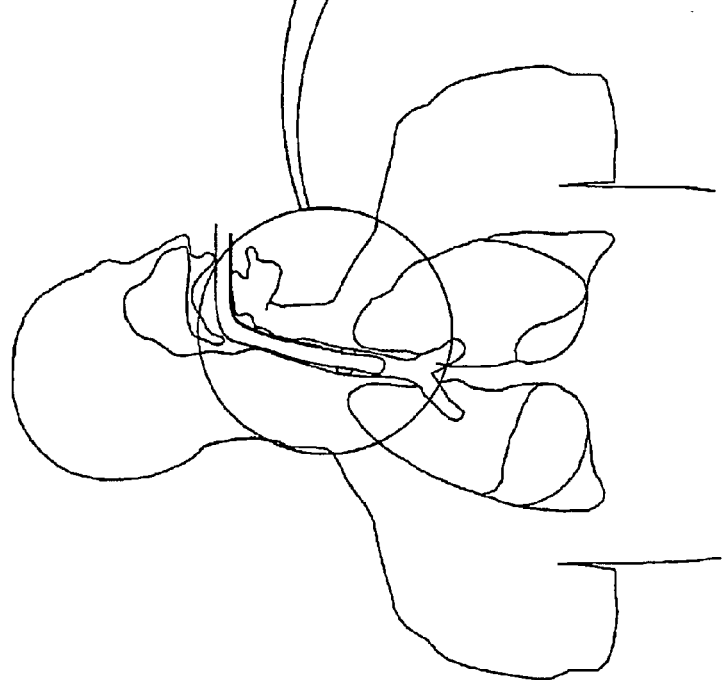

Turning to FIG. 2B, there is seen a second embodiment of the invention wherein an endotracheal tube 200 is inserted into a patient airway 211 and an inflatable cuff 212, associated therewith and inflated at a location in the patient airway 211 below the vocal cords. The endotracheal tube 200 is typically, but need not be, coupled to a ventilator 214. Cuff 212 is connected via an inflation conduit 216 to a manually operated or automatically operated cuff inflator 218.

In accordance with a preferred embodiment of the present invention shown in FIG. 2B, a carbon dioxide monitor 220 is coupled via a carbon dioxide monitor conduit 222, internal of the endotracheal tube 200 to a carbon dioxide monitoring location 224, between the cuff 212 and the vocal cords. A suctioning device 226 is also coupled to the conduit 222 for suctioning secretions at a suctioning location, which in this embodiment is identical to the carbon dioxide monitoring location 224.

Turning to FIG. 2C, there is seen a third embodiment of the invention wherein an endotracheal tube 300 is inserted into a patient airway 311 and an inflatable cuff 312, associated therewith and inflated at a location in the patient airway 311 below the vocal cords. The endotracheal tube 300 is typically, but need not be, coupled to a ventilator 314. Cuff 312 is connected via an inflation conduit 316 to a manually operated or automatically operated cuff inflator 318.

In accordance with a preferred embodiment of the present invention shown in FIG. 2C, a carbon dioxide monitor 320 is coupled via a carbon dioxide monitor conduit 322, exterior of the endotracheal tube 300, to a carbon dioxide monitoring location 324, between the cuff 312 and the vocal cords.

In this embodiment, a suctioning device 326 is coupled to a separate suctioning conduit 328, also external of the endotracheal tube 300, for suctioning secretions at a suctioning location 330, which is preferably upstream of the carbon dioxide monitoring location 324.

Figure 2D:
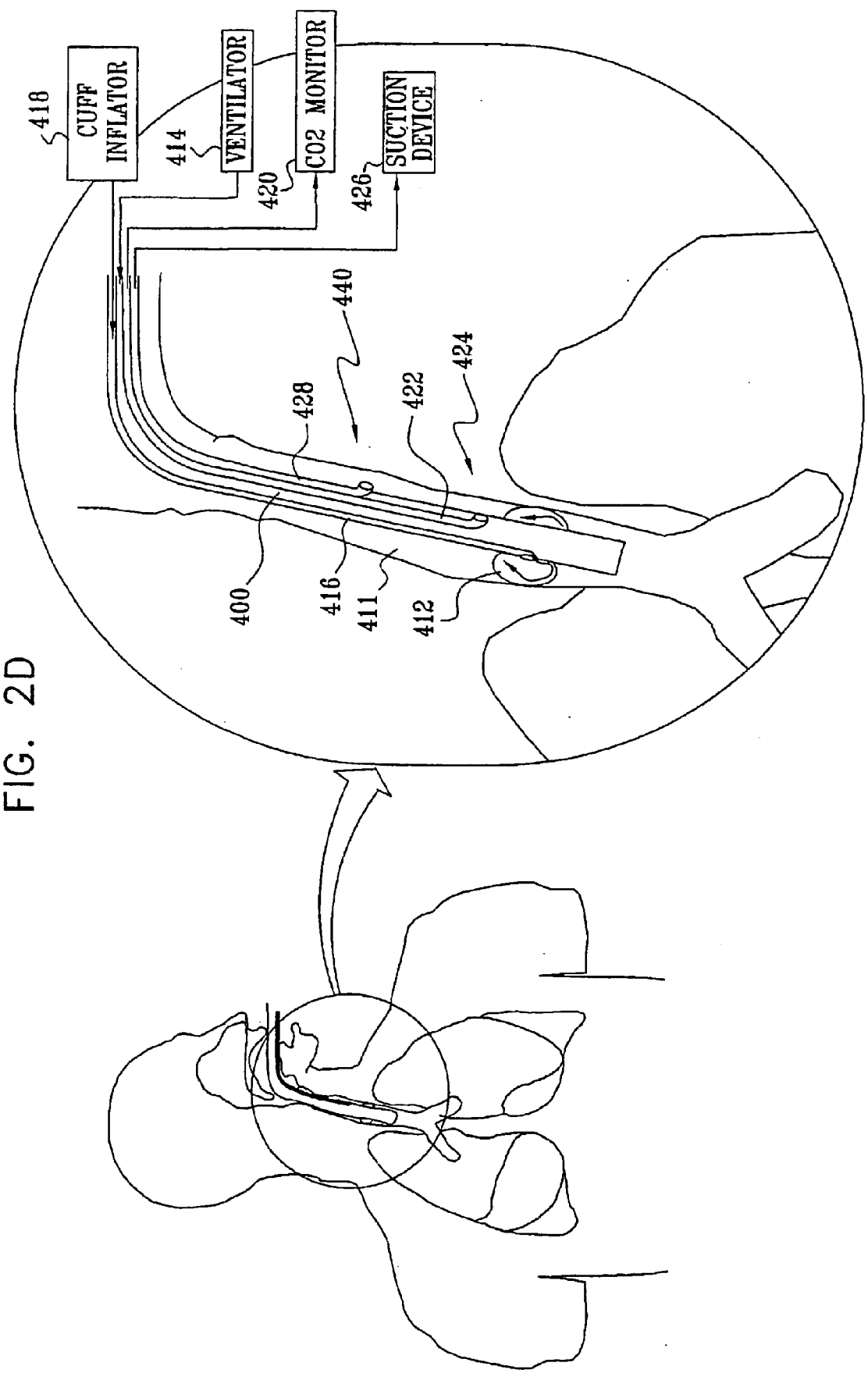

Turning to FIG. 2D, there is seen a fourth embodiment of the invention wherein an endotracheal tube 400 is inserted into a patient airway 411 and an inflatable cuff 412, associated therewith and inflated at a location in the patient airway 411 below the vocal cords. The endotracheal tube 400 is typically, but need not be, coupled to a ventilator 414. Cuff 412 is connected via an inflation conduit 416 to a manually operated or automatically operated cuff inflator 418.

In accordance with a preferred embodiment of the present invention shown in FIG. 2D, a carbon dioxide monitor 420 is coupled via a carbon dioxide monitor conduit 422, interior of the endotracheal tube 400, to a carbon dioxide monitoring location 424, between the cuff 412 and the vocal cords.

In this embodiment, a suctioning device 426 is coupled to a separate suctioning conduit 428, also internal of the endotracheal tube 400, for suctioning secretions at a suctioning location 440, which is preferably upstream of the carbon dioxide monitoring location 424.

It will be appreciated by persons skilled in the art that the present invention is not limited by what has been particularly shown and described hereinabove. Rather the scope of the present invention includes both combinations and subcombinations of the various features described hereinabove as well as variations and modifications which would occur to persons skilled in the art upon reading the specification and which are not in the prior art.

What is claimed is:

1. An intubation method comprising:

inserting an endotracheal tube into a patient airway;

inflating a cuff associated with the endotracheal tube at a location in the patient airway below the vocal cords;

monitoring carbon dioxide concentration in the patient airway at a carbon dioxide monitoring location in the patient airway above the cuff; and adjusting inflation of the cuff based at least in part on said monitoring in order that the cuff inflation generally prevents leakage of carbon dioxide past the cuff.

2. An intubation method according to claim 1 and wherein inflation of the cuff is adjusted to provide a minimum inflation pressure which prevents leakage of carbon dioxide past the cuff.

3. An intubation method according to claim 1 and also comprising suctioning secretions at a suctioning location in the patient airway above the cuff.

4. An intubation method according to claim 3 and wherein said suctioning location is located between the cuff and the carbon dioxide monitoring location.

5. An intubation method according to claim 1 wherein said adjusting inflation is performed by medical personnel based on information received from said carbon dioxide monitoring.

6. An intubation method according to claim 1 wherein said adjusting inflation is performed automatically based on information received from said carbon dioxide monitoring.

7. An intubation method according to claim 1 and also comprising inserting into the patient airway a carbon dioxide monitoring conduit extending to said carbon dioxide monitoring location.

8. An intubation method according to claim 3 and also comprising inserting into the patient airway a suctioning conduit extending to said suctioning location.

9. An intubation method according to claim 7 and wherein said carbon dioxide monitoring conduit also serves as a suctioning conduit extending to a suctioning location.

10. An intubation method according to claim 1 and wherein said inserting an endotracheal tube into a patient airway includes inserting at least one of a carbon dioxide monitoring conduit and a suctioning conduit disposed therewithin.

11. An intubation system comprising:
    an endotracheal tube adapted for insertion into a patient airway;
    an inflatable cuff associated with the endotracheal tube and arranged to be located at a location in the patient airway below the vocal cords;
    a carbon dioxide monitor operative to monitor carbon dioxide concentration in the patient airway at a carbon dioxide monitoring location in the patient airway above the cuff; and
    an inflatable cuff inflator operative for enabling adjustment of inflation of the cuff based at least in part on an output from said carbon dioxide monitor in order that the cuff inflation generally prevents leakage of carbon dioxide past the cuff.

12. An intubation system according to claim 11 and wherein said inflator comprises an adaptive inflator which is operative to inflate said cuff to a minimum inflation pressure which prevents leakage of carbon dioxide past the cuff.

13. An intubation system according to claim 11 and also comprising a suctioner operative for suctioning secretions at a suctioning location in the patient airway above the cuff.

14. An intubation system according to claim 13 and wherein said suctioning location is located between the cuff and the carbon dioxide monitoring location.

15. An intubation system according to claim 11 and also comprising:
    a carbon dioxide monitoring conduit coupled to said carbon dioxide monitor and extending therefrom to said carbon dioxide monitoring location.

16. An intubation system according to claim 15 and wherein said carbon dioxide monitoring conduit also serves as a suctioning conduit and also couples a suctioner operative for suctioning secretions to a suctioning location in the patient airway above the cuff.

17. An intubation system according to claim 15 and also comprising a suctioning conduit which couples a suctioner operative for suctioning secretions to a suctioning location in the patient airway above the cuff.

18. An intubation system according to claim 16 and wherein said suctioning location is located upstream of said carbon dioxide monitoring location.

19. An intubation system according to claim 17 and wherein at least one of said carbon dioxide monitoring conduit and said suctioning conduit are located internally of said endotracheal tube.

20. An intubation system according to claim 17 and wherein at least one of said carbon dioxide monitoring conduit and said suctioning conduit are located externally of said endotracheal tube.

21. An intubation system according to claim 17 and wherein both said carbon dioxide monitoring conduit and said suctioning conduit are located internally of said endotracheal tube.

22. An intubation system according to claim 17 and wherein both said carbon dioxide monitoring conduit and said suctioning conduit are located externally of said endotracheal tube.

* * * * *